US009993204B2

(12) United States Patent
Romesburg

(10) Patent No.: US 9,993,204 B2
(45) Date of Patent: Jun. 12, 2018

(54) CADENCE DETECTION BASED ON INERTIAL HARMONICS

(71) Applicant: Valencell, Inc., Raleigh, NC (US)

(72) Inventor: Eric Douglas Romesburg, Chapel Hill, NC (US)

(73) Assignee: Valencell, Inc., Raleigh, NC (US)

( * ) Notice: Subject to any disclaimer, the term of this patent is extended or adjusted under 35 U.S.C. 154(b) by 92 days.

(21) Appl. No.: 14/655,992

(22) PCT Filed: Jan. 6, 2014

(86) PCT No.: PCT/US2014/010326
§ 371 (c)(1),
(2) Date: Jun. 26, 2015

(87) PCT Pub. No.: WO2014/109982
PCT Pub. Date: Jul. 17, 2014

(65) Prior Publication Data
US 2015/0366509 A1    Dec. 24, 2015

Related U.S. Application Data
(60) Provisional application No. 61/750,490, filed on Jan. 9, 2013.

(51) Int. Cl.
*A61B 5/00* (2006.01)
*A61B 5/11* (2006.01)
*G01C 22/00* (2006.01)

(52) U.S. Cl.
CPC ............... *A61B 5/721* (2013.01); *A61B 5/11* (2013.01); *A61B 5/112* (2013.01); *A61B 5/6817* (2013.01);
(Continued)

(58) Field of Classification Search
None
See application file for complete search history.

(56) References Cited

U.S. PATENT DOCUMENTS 3,636,617 A    1/1972 Schmidt et al.
3,704,706 A    12/1972 Herczfeld et al.
(Continued)

FOREIGN PATENT DOCUMENTS

CN    1545979 A    11/2004
EP    0729726 A2    9/1996
(Continued)

OTHER PUBLICATIONS

Han et al. "Artifacts in wearable photoplethysmographs during daily life motions and their reduction with least mean square based active noise cancellation method," Computers in Biology and Medicine 42 (2012), Published Dec. 27, 2011, Elsevier Ltd., pp. 387-393.
(Continued)

*Primary Examiner* — Matthew Kremer
(74) *Attorney, Agent, or Firm* — Coats & Bennett, PLLC

(57) ABSTRACT

The method and apparatus disclosed herein determine a user cadence from the output of an inertial sensor mounted to or proximate the user's body. In general, the disclosed cadence measurement system determines the user cadence based on frequency measurements acquired from an inertial signal output by the inertial sensor. More particularly, a cadence measurement system determines a user cadence from an inertial signal generated by an inertial sensor, where the inertial signal comprises one or more frequency components. The cadence measurement system determines a peak frequency of the inertial signal, where the peak frequency corresponds to the frequency component of the inertial signal having the largest amplitude. After applying the peak frequency to one or more frequency threshold comparisons,
(Continued)

the cadence measurement system determines the user cadence based on the peak frequency and the frequency threshold comparison(s).

18 Claims, 6 Drawing Sheets

(52) U.S. Cl.
CPC .......... *A61B 5/7235* (2013.01); *A61B 5/7246* (2013.01); *A61B 5/7278* (2013.01); *A61B 2562/028* (2013.01); *A61B 2562/0214* (2013.01); *A61B 2562/0219* (2013.01); *A61B 2562/0233* (2013.01); *G01C 22/006* (2013.01)

(56) References Cited

U.S. PATENT DOCUMENTS

| | | | |
|---|---|---|---|
| 4,672,976 A | 6/1987 | Kroll | |
| 4,952,928 A | 8/1990 | Carroll et al. | |
| 4,955,379 A | 9/1990 | Hall | |
| 5,139,025 A | 8/1992 | Lewis et al. | |
| 5,243,992 A | 9/1993 | Eckerle et al. | |
| 5,297,548 A | 3/1994 | Pologe | |
| 5,299,570 A | 4/1994 | Hatschek | |
| 5,448,082 A | 9/1995 | Kim | |
| 5,482,036 A | 1/1996 | Diab et al. | |
| 5,494,043 A | 2/1996 | O'Sullivan et al. | |
| 5,503,016 A | 3/1996 | Koen | |
| 5,575,284 A | 11/1996 | Athan et al. | |
| 5,673,692 A | 10/1997 | Schulze et al. | |
| 5,807,267 A | 11/1998 | Bryars et al. | |
| 5,846,190 A | 12/1998 | Woehrle | |
| 5,853,005 A | 12/1998 | Scanlon | |
| 5,906,582 A | 5/1999 | Kondo et al. | |
| 5,908,396 A * | 6/1999 | Hayakawa ........... | G01C 22/006 600/503 |
| 5,941,837 A | 8/1999 | Amano et al. | |
| 5,954,644 A | 9/1999 | Dettling et al. | |
| 5,964,701 A | 10/1999 | Asada et al. | |
| 6,022,748 A | 2/2000 | Charych et al. | |
| 6,042,549 A * | 3/2000 | Amano ............... | A61B 5/02438 600/500 |
| 6,067,462 A | 5/2000 | Diab et al. | |
| 6,198,394 B1 | 3/2001 | Jacobsen et al. | |
| 6,241,684 B1 | 6/2001 | Amano et al. | |
| 6,267,721 B1 | 7/2001 | Welles | |
| 6,393,311 B1 | 5/2002 | Edgar, Jr. et al. | |
| 6,443,890 B1 | 9/2002 | Schulze et al. | |
| 6,527,711 B1 | 3/2003 | Stivoric et al. | |
| 6,608,562 B1 | 8/2003 | Kimura et al. | |
| 6,656,151 B1 | 12/2003 | Blatter | |
| 6,725,072 B2 | 4/2004 | Steuer et al. | |
| 6,748,254 B2 | 6/2004 | O'Neil et al. | |
| 6,995,665 B2 | 2/2006 | Appelt et al. | |
| 6,997,879 B1 | 2/2006 | Turcott | |
| 7,018,338 B2 | 3/2006 | Vetter et al. | |
| 7,113,815 B2 | 9/2006 | O'Neil et al. | |
| 7,144,375 B2 | 12/2006 | Kosuda | |
| 7,336,982 B2 | 2/2008 | Yoo | |
| 7,378,954 B2 | 5/2008 | Wendt | |
| 7,438,688 B2 | 10/2008 | Kobayashi et al. | |
| 7,539,533 B2 | 5/2009 | Tran | |
| 8,055,469 B2 | 11/2011 | Kulach et al. | |
| 8,923,941 B2 | 12/2014 | LeBoeuf et al. | |
| 9,005,129 B2 | 4/2015 | Venkatraman et al. | |
| 9,044,180 B2 | 6/2015 | LeBoeuf et al. | |
| 2002/0013538 A1 | 1/2002 | Teller | |
| 2003/0065269 A1 | 4/2003 | Vetter et al. | |
| 2003/0109791 A1 | 6/2003 | Kondo et al. | |
| 2003/0176815 A1 | 9/2003 | Baba et al. | |
| 2003/0233051 A1 | 12/2003 | Verjus et al. | |
| 2003/0236647 A1 | 12/2003 | Yoon et al. | |
| 2004/0004547 A1 | 1/2004 | Appelt et al. | |
| 2004/0039254 A1 | 2/2004 | Stivoric et al. | |
| 2004/0054291 A1 | 3/2004 | Schulz et al. | |
| 2004/0059236 A1 | 3/2004 | Margulies et al. | |
| 2004/0186387 A1 | 9/2004 | Kosuda et al. | |
| 2004/0186695 A1 * | 9/2004 | Aoshima ............... | G01C 22/006 702/190 |
| 2004/0178913 A1 | 11/2004 | Penuela et al. | |
| 2004/0236233 A1 | 11/2004 | Kosuda et al. | |
| 2004/0242976 A1 | 12/2004 | Abreu | |
| 2004/0254501 A1 | 12/2004 | Mault | |
| 2005/0007582 A1 | 1/2005 | Villers et al. | |
| 2005/0043652 A1 * | 2/2005 | Lovett ................... | A61B 5/00 600/595 |
| 2005/0059870 A1 | 3/2005 | Aceti | |
| 2005/0192516 A1 | 9/2005 | Takiguchi et al. | |
| 2005/0209516 A1 | 9/2005 | Fraden | |
| 2005/0228463 A1 | 10/2005 | Mac et al. | |
| 2005/0245839 A1 | 11/2005 | Stivoric et al. | |
| 2006/0064037 A1 | 3/2006 | Shalon et al. | |
| 2006/0084879 A1 | 3/2006 | Nazarian et al. | |
| 2006/0258927 A1 * | 11/2006 | Edgar, Jr. ........... | A61B 5/14551 600/336 |
| 2007/0016086 A1 | 1/2007 | Inukai et al. | |
| 2007/0116314 A1 | 5/2007 | Grilliot et al. | |
| 2007/0135717 A1 | 6/2007 | Uenishi et al. | |
| 2008/0076972 A1 | 3/2008 | Dorogusker et al. | |
| 2008/0081972 A1 | 4/2008 | Debreczeny | |
| 2008/0132798 A1 | 6/2008 | Hong et al. | |
| 2008/0146890 A1 | 6/2008 | LeBoeuf et al. | |
| 2008/0154098 A1 | 6/2008 | Morris et al. | |
| 2008/0177162 A1 | 7/2008 | Bae et al. | |
| 2008/0269625 A1 | 10/2008 | Halperin et al. | |
| 2009/0010461 A1 | 1/2009 | Klinghult et al. | |
| 2009/0023556 A1 | 1/2009 | Daly et al. | |
| 2009/0097689 A1 | 4/2009 | Prest et al. | |
| 2009/0105556 A1 | 4/2009 | Fricke et al. | |
| 2009/0112111 A1 | 4/2009 | Shimizu et al. | |
| 2009/0131761 A1 | 5/2009 | Moroney, III et al. | |
| 2009/0281435 A1 | 11/2009 | Ahmed et al. | |
| 2009/0306736 A1 | 12/2009 | Dobak, III | |
| 2010/0189209 A1 | 7/2010 | O'Rourke | |
| 2012/0197093 A1 | 8/2012 | LeBoeuf et al. | |
| 2012/0303319 A1 | 11/2012 | Kirkeby | |
| 2013/0006583 A1 | 1/2013 | Weast et al. | |

FOREIGN PATENT DOCUMENTS

| | | |
|---|---|---|
| EP | 2229880 A1 | 9/2010 |
| EP | 2182839 B1 | 10/2011 |
| JP | H0258039 A | 9/1998 |
| JP | 2004283228 A | 10/2004 |
| JP | 2004358271 A | 12/2004 |
| WO | 0021435 A1 | 4/2000 |
| WO | 2005010568 A2 | 2/2005 |
| WO | 2007013054 A1 | 2/2007 |
| WO | 2007122375 A2 | 11/2007 |
| WO | 2011105914 A1 | 1/2011 |
| WO | 2013038296 A1 | 3/2013 |
| WO | 2013109389 A1 | 7/2013 |
| WO | 2013109390 A1 | 7/2013 |

OTHER PUBLICATIONS

Bumgardner, W., "Top 8 Walking Speedometers and Odometers", retrieved on Jun. 18, 2014 retrieved from internet: http://walking.about.com/od/measure/tp/speedometer.htm.

Garmin, "Running Watches Heart Rate Monitor", Swim Watch, Heart Rate Monitors Reviews, Oct. 12, 2010 retrieved from internet: http://web.archive.org/web/*/http://heartratemonitors-reviews.com/category/swim-watch/.

Declaration of Brian W. Anthony, Ph.D. in Support of Petition for Inter Partes Review of U.S. Pat. No. 9,044,180, Exhibit 1003, Petition for Inter Partes Review of U.S. Pat. No. 9,044,180; *Apple, Inc.* (Petitioner) v. *Valencell, Inc.* (Patent Owner), IPR 2017-01947, filed 15 Aug. 2-17, pp. 1-153.

Mendelson, J., et al., "Measurement Site and Photodetector Size Considerations iin Optimizing Power Consumption of a Wearable

(56) References Cited

OTHER PUBLICATIONS

Reflectance Pulse Oximeter", Proceedings of the 25th Annual International Conference of the IEEE EMBS, Engineering in Medicine and Biology Society, Cancun, Mexico, Sep. 17, 2003, pp. 1-4.
Palder, et al., "Vascular Access for Hemodialysis, Patency rates and Results of Revision", Annals of Surgery, vol. 202, No. 2, Aug. 1, 1985, pp. 1-5.
Spigulis, J., et al., "Wearable wireless photoplethysmography sensors," Biophotonics: Photonic Solutions for Better Health Care, Proceedings of SPIE, vol. 6991, May 1, 2008, pp. 1-7.
Sandberg, M., et al., "Non-invasive monitoring of muscle blood perfusion by photoplethysmography: evaluation of a new application," Acta Physiol Scand., vol. 183, No. 4, Dec. 7, 2004, pp. 335-343.
Sum, K.W., et al. "Vital Sign Monitoring for Elderly at Home: Development of a Compound Sensor for Pulse Rate and Motion," Studies in Health Technology and Informatics, Personalised Health Management Systems, IOS Press, Jan. 1, 2005, pp. 43-50.
Mendelson, Y., et al., "A Wearable Reflectance Pulse Oximeter for Remote Physiological Monitoring," Proceedings of the 28th IEEE EMBS Annual International Conference New York City, USA, Aug. 30, 2006, pp. 912-915.
Jung, W., "Chapter H: OP Amp History," OP Amp Applications Handbook, published by Newnes/Elsevier, Jan. 1, 2005, ISBN-0-7506-7844-5, pp. H.1-H.72.
Texas Instruments, "General Purpose Operational Amplifiers", SLOSS094B, Nov. 1, 1970, pp. 1-19.
Schmitt, O., "A simple differential amplifier," Review of Scientific Instruments vol. 8, No. 126, Apr. 1, 1937, American Institute of Physics, pp. 1-3, available at: http://dx.doi.org/10.1063/1.1752256.
Gray, p, et al., "Recent Advances in Monolithic Operational Amplifier Design," IEEE Transactions on Circuits and Systems, vol. CAS-21, No. 3, May 1, 1974, pp. 317-327.
Horowitz, P., et al., "The Art of Electronics," Second Edition, Cambridge University Press, Jan. 1, 1989, pp. 98-102.
Petition for Inter Partes Review of U.S. Pat. No. 9044180; *Apple, Inc.* (Petitioner) v. *Valencell, Inc.* (Patent Owner), IPR 2017-01947, filed Aug. 15, 2017, pp. 1-86.
Buchanan, T., et al., "Neuromusculoskeletal Modeling: Estimation of Muscle Forces and Joint Moments and Movements From Measurements of Neural Command," J Appl Biomech, vol. 20, No. 4, Nov. 1, 2004, pp. 1-34.
Stolwijk, J., "Mathematical Models of Thermal Regulation," Annals of the New York Academy of Sciences, vol. 335, No. 1, Jan. 1, 1980, pp. 98-106.
Wiggs, L, et al., "Sleep patterns and sleep disorders in children with autistic spectrum disorders: insights using parent report and actigraphy," Developmental Medicine and Child Neurology 2004, vol. 46, No. 6, Jan. 1, 2004, pp. 372-380.
Hastings, P.C., "Symptom burden of sleep-disordered breathing in mild-to-moderate congestive heart failure patients," European Respiratory Journal, vol. 27, No. 4, Jan. 1, 2006, pp. 748-755.
Carskadon, M., et al., "Chapter 2—Normal Human Sleep: an Overview," Monitoring and staging human sleep, from Principles and practice of sleep medicine, 5th edition, St. Louis: Elsevier Saunders, Jan. 1, 2011, pp. 1-21.
Critchley, H, "Electrodermal Responses: What Happens in the Brain," The Neuroscientist, vol. 8, No. 2, Jan. 1, 2002, pp. 132-142.
Lang, P., et al., "Looking at pictures: Affective, facial, visceral, and behavioral reactions," Psychophysiology, vol. 30, No. 3, Apr. 22, 1992, pp. 261-273.
Soleymani, M., et al., "Affective Ranking of Movie Scenes Using Physiological Signals and Content Analysis," Proc. 2nd ACM Work. Multimed. Semant., Jan. 1, 2008, pp. 1-8.
Appelhans, B., et al., "Heart Rate Variability as an Index of Regulated Emotional Responding," Review of General Psychology, vol. 10, No. 3, Sep. 15, 2005, pp. 229-240.
Postma, D.S., et al., "The natural history of chronic obstructive pulmonary disease," European Respiratory Monograph, vol. 38, Jan. 1, 2006, pp. 71-83.
Bidargaddi, N., et al., "Ambulatory monitor derived clinical measures for continuous assessment of cardiac rehabilitation patients in a community care model," Pervasive Computing Technologies for Healthcare, 2008 Second International Conference on Pervasive Computing Technovies for Healthcare, Jan. 30, 2008, pp. 1-5.
Hertzman, A., "The Blood Supply of Various Areas as Estimated by the Photoelectric Plethysmograph," Am J. Physiol, vol. 124, Issue 2, Jul. 18, 1938, pp. 328-340.
Hayes, M., et al., "Artifact reduction in photoplethysmography," Applied Optics, vol. 37, No. 31, Nov. 1, 1998, pp. 7437-7446.
Page, E., et al., "Physiological approach to monitor patients in congestive heart failure: application of a new implantable device-based system to monitor daily life activity and ventilation," Eurospace, vol. 9, May 3, 2007, pp. 687-693.
Moy, M., et al., "Free-living physical activity in COPD: Assessment with accelerometer and activity checklist," Journal of Rehabilitation Research & Development, vol. 46, No. 2, Nov. 2, 2009, pp. 277-286.
Bennett, T., et al., "Development of Implantable Devices for Continuous Ambulatory Monitoring of Central Hemodynamic Values in Heart Failure Patients," Pacing Clin Electrophysiol. Jun. 2005; vol. 28, No. 6, Jun. 1, 2005, pp. 573-584.
Allen, J., "Photoplethysmography and its application in clinical physiological measurement," Physiological Measurement, vol. 28, Feb. 20, 2007, pp. 1-39.
Webster, J.G. (ed.), "Design of Pulse Oximeters," Institute of Physics Publishing, Philadelphia, PA, Jan. 1, 1997, pp. 1-134.
Webster, J.G. (ed.), "Design of Pulse Oximeters," Institute of Physics Publishing, Philadelphia, PA, Jan. 1, 1997, pp. 135-267.
Shevchenko, Y, et al., "90th Anniversary of the Development by Nikolai S. Korotkoff of the Ascultatory Method of Measuring Blood Pressure," Circulation, vol. 94, No. 2, Jul. 15, 1996, pp. 116-118.
Han, H., et al., "Development of a wearable monitoring device with motion artifact reduced algorithm," International Conference on Control, Automation and Systems 2007, Oct. 17, 2007, Seoul, Korea, pp. 1581-1584.
Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-89.
Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-70.
Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-79.
Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-84.
Declaration of Dr. Majid Sarrafzadeh, Exhibit 1003, Petition for Inter Partes Review of U.S. Pat. No. 8,888,701; *Apple, Inc.* (Petitioner) v. *Valencell, Inc.* (Patent Owner), IPR 2017-01704, filed Jun. 30, 2017, pp. 1-109.
Declaration of Brian W. Anthony, Ph.D. in Support of Petition for Inter Partes Review of U.S. Pat. No. 8,157,730, Exhibit 1003, Petition for Inter Partes Review of U.S. Pat. No. 8,157,730; *Apple, Inc.* (Petitioner) v. *Valencell, Inc.* (Patent Owner), IPR 2017-01701, filed Jun. 30, 2017, pp. 1-138.
Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01703, filed Jun. 30, 2017, pp. 1-87.
Declaration of Dr. Majid Sarrafzadeh, Exhibit 1003, Petition for Inter Partes Review of U.S. Pat. No. 8,652,040; *Apple, Inc.* (Petitioner) v. *Valencell, Inc.* (Patent Owner), IPR 2017-01702, filed Jun. 30, 2017, pp. 1-92.
Asada, H., et al., "Mobile Monitoring with Wearable Photoplethysmographic Biosensors," IEEE Engineering in Medicine and Biology Magazine, May/Jun. 2003 Issue, May 1, 2003, pp. 28-40.
Wang, L. et al. "Multichannel Reflective PPG Earpiece Sensor with Passive Motion Cancellation," IEEE Transactions on Biomedical Circuits and Systems, vol. 1, No. 4, Dec. 1, 2007, pp. 235-241.

(56) References Cited

OTHER PUBLICATIONS

Poh, Ming-Zher et al., "Non-contact, automated cardiac pulse measurements using video imaging and blind source separation." Optics Express, vol. 18, No. 10, May 7, 2010, pp. 1-13.
Wise, K., "Integrated sensors, MEMS, and microsystems: Reflections on a fantastic voyage," Sensors and Actuators A, vol. 136, Feb. 5, 2007, pp. 39-50.
Gigoi, B.P., et al., "Integration Technology for MEMS Automotive Sensors," 28th Annual Conference of the IEEE, Jan. 1, 2002, pp. 2712-2717.
Ko, W., "Trends and frontiers of MEMS," Sensors and Actuators A, vol. 136, Feb. 1, 2007, pp. 62-67.
Barbour, N., "Inertial Sensor Technology Trends," IEEE Sensors Journal, vol. 1, No. 4, Dec. 1, 2001, pp. 332-339.
Vigario, R., "Independent Component Approach to the Analysis of EEG and MEG Recordings," IEEE Transactions on Biomedical Engineering, vol. 47, No. 5, May 1, 2000, pp. 589-593.
Mayer-Kress, G., "Localized Measures for Nonstationary Time-Series of Physiological Data," Integr. Physiol. Behav. Sci., vol. 29, No. 3, Jul. 1, 1994, pp. 205-210.
Shaw, G.A., et al., "Warfighter Physiological and Environmental Monitoring: A Study for the U.S. Army Research Institute in Environmental Medicine and the Soldier Systems Center," Lincoln Laboratory, Massachusetts Institute of Technology, Lexington, MA., Nov. 1, 2004, pp. 1-128.
Laguna, P., et al., "Power Spectral Density of Unevenly Sampled Data by Least-Square Analysis: Performance and Application to Heart Rate Signals," IEEE Transactions on Biomedical Engineering, vol. 45, No. 6, Jun. 1, 1998, pp. 698-715.
Richardson, J.E., "Physiological Responses of Firefighters Wearing Level 3 Chemical Protective Suits While Working in Controlled Hot Environments," J. Occup. Environ. Med., vol. 43, No. 12, Dec. 1, 2001, pp. 1064-1072.
Scanlon, M., "Acoustic Sensors in the Helmet Detect Voice and Physiology," Proceedings of SPIE, vol. 5071, Jan. 1, 2003, pp. 41-51.
Arnold, M., et al., "Adaptive AR Modeling of Nonstationary Time Series by Means of Kalman Filtering," IEEE Transactions on Biomedical Engineering, vol. 45, No. 5, May 1, 1998, pp. 553-562.
Yan, Y., et al., "Reduction of motion artifact in pulse oximetry by smoothed pseudo Wigner-Ville distribution," Journal of NeuroEngineering and Rehabilitation, vol. 2, No. 3, Mar. 1, 2005, pp. 1-9.
Lee, C.M., et al., "Reduction of Motion Artifacts from Photoplethysmographic Recordings Using a Wavelet Denoising Approach," IEEE EMBS Asian-Pacific Conference on Biomedical Engineering, Jan. 1, 2003, pp. 194-195.
Foo, J.Y.A., "Comparison of wavelet transformation and adaptive filtering in restoring artefact-induced time-related measurement," Biomedical Signal Processing and Control vol. 1, No. 1 (2006), Mar. 24, 2006, pp. 93-98.
Wood, L., et al., "Active Motion Artifact Reduction for Wearable Sensors Using Laguerre Expansion and Signal Separation," Proceedings of the 2005 IEEE Engineering in Medicine and Biology 27th Annual Conference, Shanghai, China, Sep. 1, 2005, pp. 3571-3574.
Cacioppo, J., "Inferring Psychological Significance From Physiological Signals," American Psychologist, vol. 45, No. 1, American Psychological Association, Jan. 1, 1990, pp. 16-28.
Rhee, S., et al., "Artifact-Resistant Power-Efficient Design of Finger-Ring Plethysmographic Sensors," IEEE Transactions on Biomedical Engineering, vol. 48, No. 7, Jul. 1, 2001, pp. 795-805.
Wagner, J., et al., "From Physiological Signals to Emotions: Implementing and Comparing Selected Methods for Feature Extraction and Classification," IEEE Int. Conf. Multimedia and Expo, Jan. 1, 2005, pp. 1-4.
Parkka, J., et al., "Activity Classification Using Realistic Data From Wearable Sensors," IEEE Transactions on Information Technology in Biomedicine, vol. 10, No. 1, Jan. 1, 2006, pp. 119-128.

Georgoulas, G., et al., "Predicting the Risk of Metabolic Acidosis for Newborns Based on Fetal Heart Rate Signal classification Using Support Vector Machines," IEEE Transactions on Biomedical Engineering, vol. 53, No. 5, May 1, 2006, pp. 875-884.
Liao, W., et al., "A Real-Time Human Stress Monitoring System Using Dynamic Bayesian Network," Proceedings of the 2005 IEEE Computer Society Conference on Computer Vision and Pattern Recognition, Jan. 1, 2005, pp. 1-8.
Moy, M., et al., "Accuracy of uniaxial accelerometer in chronic obstructive pulmonary disease," Journal of Rehabilitation Research and Development, vol. 45, No. 4, Nov. 4, 2008, pp. 611-618.
Moy, M., et al., "Ambulatory Monitoring of Cumulative Free-Living Activity," IEEE Engineering in Medicine and Biology Magazine May/Jun. 2003, May 1, 2003, pp. 89-95.
Ricke, Ad, et al. "Automatic Segmentation of Heart Sound Signals Using Hidden Markov Models," IEEE Computers in Cardiology 2005; vol. 32, Jan. 1, 2005, pp. 953-956.
Acharya, R., et al., "Classification of cardiac abnormalities using heart rate signals," Medical and Biological Engineering and Computing 2004, vol. 42, No. 3, Jan. 1, 2004, pp. 288-293.
Allen, F., et al., "Classification of a known sequence of motions and postures from accelerometry data using adapted Gaussian mixture models," Institute of Physics Publishing Physiological Measurement, vol. 27, No. 10, Jul. 25, 2006, pp. 935-951.
Lee, J., et al., "Design of filter to reject motion artifact of pulse oximetry," Computer Standards & Interfaces, vol. 26 (2004), Jul. 4, 2003, pp. 241-249.
Rezek, I.A., et al., "Stochastic Complexity Measures for Physiological Signal Analysis," IEEE Transactions on Biomedical Engineering, vol. 45, No. 9, Sep. 1, 1998, pp. 1186-1191.
Gibbs, P., et al., "Active motion artifact cancellation for wearable health monitoring sensors using collocated MEMS accelerometers," Smart Struct. Mater., International Society for Optics and Photonics, Jan. 1, 2005, pp. 1-9.
Merletti, R., et al., "Advances in processing of surface myoelectric signals: Part 1," Medical and Biological Engineering and Computing, vol. 33, No. 3, May 1, 1995, pp. 362-372.
Asada, H., et al., "Active Noise Cancellation Using MEMS Accelerometers for Motion-Tolerant Wearable Bio-Sensors," Proceedings of the 26th Annual International Conference of the IEEE EMBS, San Francisco, CA, USA, Sep. 1, 2004, pp. 2157-2160.
Newman, A., et al., "Sleep Disturbance, Psychosocial Correlates, and Cardiovascular Disease in 5201 Older Adults: The Cardiovascular Health Study," Journal of American Geriatric Society, vol. 45, No. 1, Jan. 1, 1997, pp. 1-7.
Chan, K.W., et al., "Adaptive Reduction of Motion Artifact from Photoplethysmographic Recordings using a Variable Step-Size LMS Filter," IEEE, Sensors, Jun. 1, 2002, pp. 1342-1346.
Dew, M.A., et al., "Healthy Older Adults' Sleep Predicts All-Cause Mortality at 4 to 19 Years of Follow-Up," Psychosomatic Medicine, vol. 65, Jan. 1, 2003, pp. 63-73.
Gibbs, P., et al., "Reducing Motion Artifact in Wearable Bio-Sensors Using MEMS Accelerometers for Active Noise Cancellation," IEEE American Control Conference, Jun. 1, 2005, pp. 1581-1586.
Yang, B-H, et al., "Development of the ring sensor for healthcare automation," Robotics and Autonomous Systems, vol. 30. Jan. 1, 2000, pp. 273-281.
Healey, J., et al., "Detecting Stress During Real-World Driving Tasks Using Physiological Sensors," IEEE Transactions on Intelligent Transportation Systems, vol. 6, No. 2, June 1, 2005, pp. 156-166.
Hayes, M.J., et al., "A New Method for Pulse Oximetry Possessing Inherent Insensitivity to Artifact," IEEE Transactions on Biomedical Engineering, vol. 48, No. 4, Apr. 1, 2001, pp. 452-461.
Wilson, G., et al., "An Analysis of Mental Workload in Pilots During Flight Using Multiple Psychophysiological Measures," The International Journal of Aviation Psychology, vol. 12, No. 1, May 1, 2001, pp. 3-18.
Baddeley, A.D., "Selective Attention and Performance in Dangerous Environments," HPEE, vol. 5, No. 1, Oct. 1, 2000, pp. 86-91.
Wilson, G.F., et al., "Performance Enhancement with Real-time Physiologically Controlled Adaptative Aiding," Proceedings of the IEA 2000 / HFES 2000 Congress, vol. 44, Jul. 30, 2000, pp. 61-64.

(56) References Cited

OTHER PUBLICATIONS

Skinner, M.J., et al., "Workload Issues in Military Tactical Airlift," The International Journal of Aviation Psychology, vol. 12, No. 1, May 1, 2001, pp. 79-93.
Helander, M., "Applicability of Drivers' Electrodermal Response to the Design of the Traffic Environment," Journal of Applied Psychology, vol. 63, No. 4, Jan. 18, 1978, pp. 481-488.
Perala, C.H., "Galvanic Skin Response as a Measure of Soldier Stress," Army Research Laboratory, ARL-TR-4114, May 1, 2007, pp. 1-35.
Zhai, J. et al., "Stress Detection in Computer Users Based on Digital Signal Processing of Noninvasive Physiological Variables," Conf Proc IEEE Eng Med Biol Soc., New York, NY, Aug. 31, 2006; pp. 1355-1358.
Zhai, J. et al., "Stress Recognition Using Non-invasive Technology," FLAIRS Conference, Melbourne Beach, Florida, May 11, 2006, AAAI Press, pp. 395-401.
Endler, J., "Signals, Signal Conditions, and the Direction of Evolution," The American Naturalist, vol. 139, Supplement, Mar. 1, 1992, pp. S125-S153.
Sadeh, A., "The role of actigraphy in sleep medicine," Sleep Medicine Reviews, vol. 6, No. 2, Jan. 1, 2002, pp. 113-124.

\* cited by examiner

CADENCE DETECTION BASED ON INERTIAL HARMONICS

BACKGROUND

Personal health monitors provide users with the ability to monitor their overall health and fitness by enabling the user to monitor heart rate or other physiological information during exercise, athletic training, rest, daily life activities, physical therapy, etc. Such devices are becoming increasingly popular as they become smaller and more portable.

In addition to providing bodily performance information such as heart rate and breathing rate, a personal health monitor may also provide performance information about the current activity, e.g., duration, distance, cadence, etc. As with many parameters, however, the accurate determination of such information may be compromised by noise.

A user's cadence enables the user to monitor their current performance relative to their personal goals, and therefore represents a particularly useful piece of activity performance information. As used herein, a cadence represents the number of repetitions per minute. For example, when the user is moving on foot, the cadence represents the number of foot repetitions or steps per minute. When the user is moving on wheels, the cadence represents the number of cycle repetitions (e.g., crank or pedal revolutions) per minute.

Conventional devices may monitor the cycling cadence, for example, using a cyclocomputer. A sensor system mounted to the crank arm and frame of the bicycle counts the number of wheel rotations per minute to determine the cycling cadence. While such devices are useful and reasonably accurate, they are cumbersome and cannot easily be used with multiple bicycles. Further, such devices cannot provide an accurate estimate of the number of steps per minute taken, e.g., by a runner. Thus, there remains a need for more portable devices capable of measuring a user cadence in a wide variety of scenarios.

SUMMARY

The method and apparatus disclosed herein determine a user cadence from the output of an inertial sensor mounted to or proximate the user's body, e.g., disposed in an ear bud worn by the user. In general, a cadence measurement system determines the cadence based on frequency measurements acquired from an inertial signal output by the inertial sensor.

An exemplary method determines a user cadence from an inertial signal generated by an inertial sensor, where the inertial signal comprises one or more frequency components. The method determines a peak frequency of the inertial signal, where the peak frequency corresponds to the frequency component of the inertial signal having the largest amplitude. After applying the peak frequency to one or more frequency threshold comparisons, the user cadence is determined based on the peak frequency and the one or more frequency threshold comparisons.

In one embodiment, a cadence measurement system determines the user cadence. The cadence measurement system comprises an inertial sensor and a cadence circuit. The inertial sensor is configured to output an inertial signal comprising one or more frequency components. The cadence circuit is operatively connected to the inertial sensor, and comprises a peak frequency circuit, a comparison circuit, and a cadence processor circuit. The peak frequency circuit is configured to determine a peak frequency of the inertial signal, where the peak frequency corresponds to the frequency component of the inertial signal having the largest amplitude. The comparison circuit is configured to apply the peak frequency to one or more frequency threshold comparisons. The cadence processor circuit is configured to determine the user cadence based on the peak frequency and the one or more frequency threshold comparisons.

DETAILED DESCRIPTION

Figure 1:
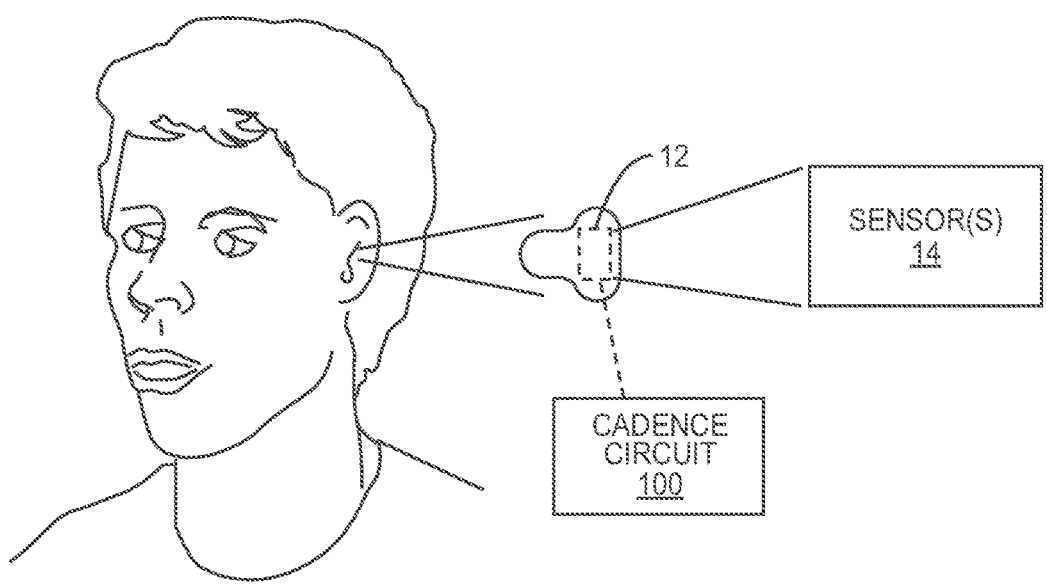
FIG. 1 shows an exemplary cadence measurement system disposed in an ear bud.

The cadence measurement technique disclosed herein provides an accurate measurement of a user's cadence based on a signal provided by an inertial sensor disposed proximate a user's body. FIG. 1 shows part of an exemplary cadence measurement system 10, where one or more sensors 14 are disposed in an ear bud 12, and a cadence circuit 100 is operatively connected to the sensor(s) 14, e.g., via a wired or wireless connection. The cadence circuit 100 may be secured to the user, e.g., via a clip. The ear bud 12 may comprise a wireless or wired ear bud that communicatively couples to a remote device, e.g., a music player, a smart phone, a personal data assistant, etc. While not required, it will be appreciated that the cadence circuit 100 may be disposed in the remote device. While FIG. 1 shows the sensor(s) 14 as being part of an ear bud 12, it will be appreciated that the sensor(s) 14 may be disposed in any device that secures to the body of a user, e.g., a device that secures to an ear, finger, toe, limb, ankle, wrist, nose, etc. In some embodiments, the device may comprise a patch, e.g., a bandage, designed to attach the system 10 to any desired location on the user's body. While FIG. 1 shows the cadence circuit 100 as being separate from the ear bud 12, it will be appreciated that the cadence circuit 100 may be disposed in the ear bud 12

The cadence measurement system 10 measures the user's cadence, and outputs the cadence to the user and/or to other processing functions or elements. As used herein, the "cadence" refers to the number of repetitions or complete cycles per minute. Exemplary user cadences include, but are not limited to, a step rate (e.g., the number of steps or foot repetitions per minute), a cycle rate (e.g., the number of pedaling cycles or cycle revolutions per minute), a repetition rate (e.g., with respect to lifting weights), etc. It will be appreciated that a step rate cadence may represent the user's cadence while walking, running, doing aerobics, climbing stairs, etc. Further, it will be appreciated that the cadence measurement system may be used with any mobile animals having one or more limbs that facilitate and/or enable the animal's movement, or with machinery, e.g., a walking robot. Exemplary animals include, but are not limited to, biped animals (e.g., humans, birds, etc.) and quadruped animals (e.g., dogs, horses, etc.).

Figure 2:
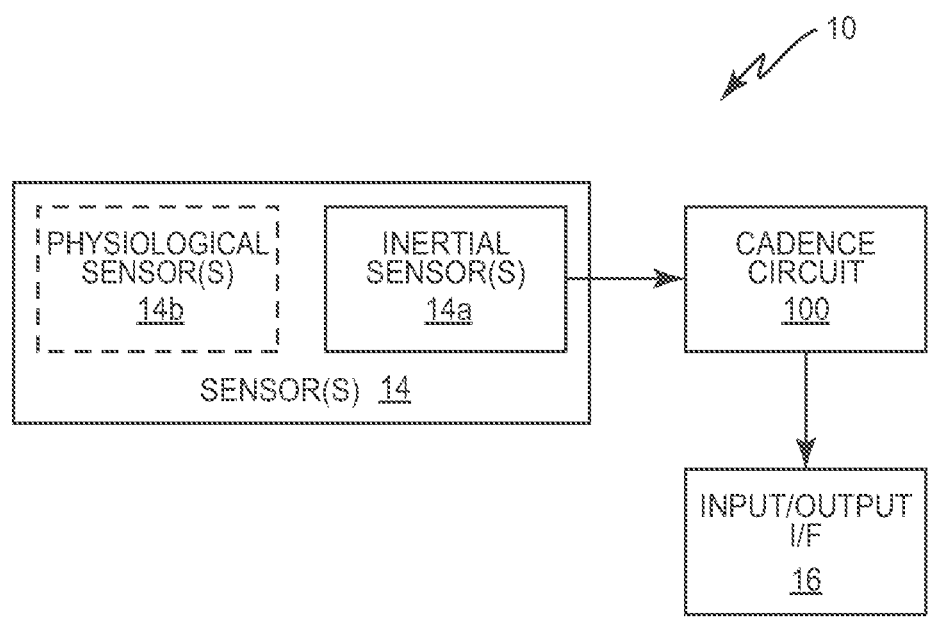
FIG. 2 shows a block diagram of an exemplary cadence measurement system.
Figure 3:
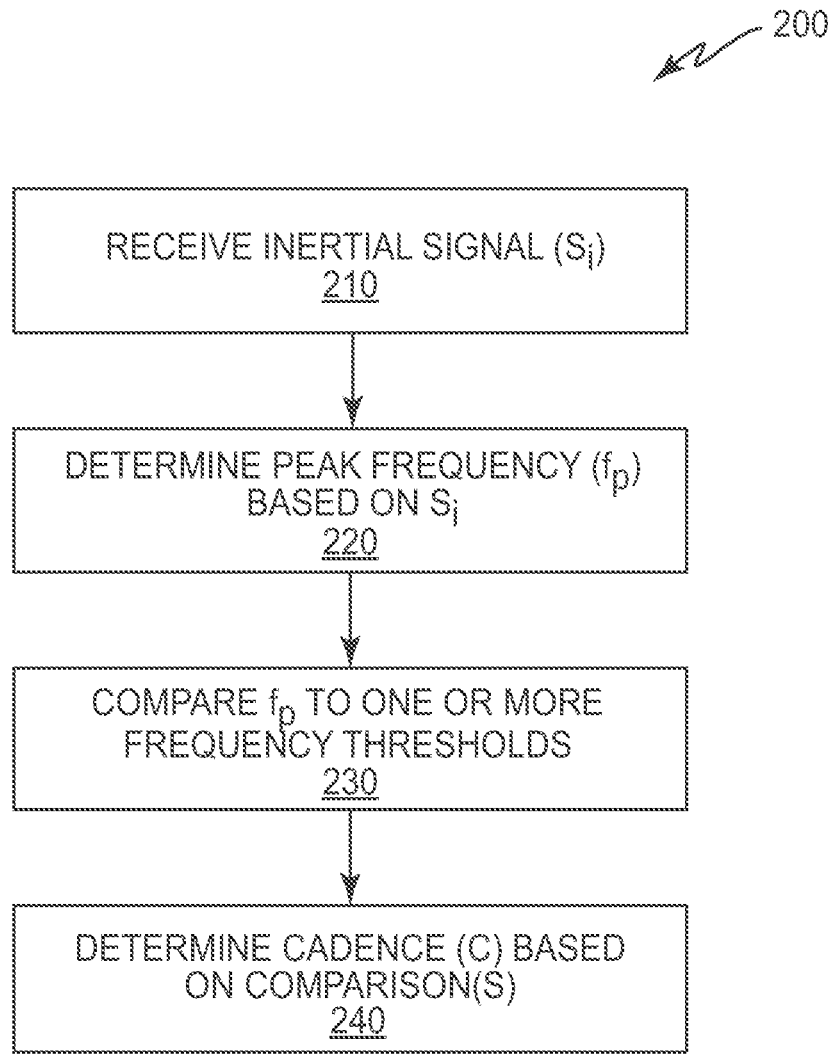
FIG. 3 shows an exemplary process for determining the cadence from data provided by an inertial sensor.

FIG. 2 shows a block diagram of an exemplary cadence measurement system 10 according to one exemplary embodiment. System 10 comprises the cadence circuit 100 coupled to one or more sensors 14 and an input/output interface 16, where the sensor(s) 14 include at least one inertial sensor 14a, and an optional physiological sensor 14b. It will be appreciated that the inertial sensor 14a may incorporate a physiological sensor or physiological sensor capabilities. Inertial sensor 14a is configured to sense energy, e.g., motion, external to the system 10, and to output an inertial signal $S_i$ representative of the sensed energy. The inertial sensor 14a may comprise a single axis sensor or a multiple axis sensor. Exemplary inertial sensors 14a include but are not limited to accelerometers, Micro-Electro-Mechanical System (MEMS) devices, gyroscopes, optical sensors, an opto-mechanical sensor, a blocked channel sensor, a capacitive sensor, and a piezo sensor. When the inertial sensor 14a comprises a multiple axis sensor, frequency and power information from each axis may be combined or otherwise evaluated to determine the desired information, e.g., the peak frequency and the inertial power. For example, the spectral magnitude may be determined for each axis, where a maximum one of the spectral magnitudes, a sum of the squares, a maximum of the absolute squares, a sum of the absolute values, a maximum of the absolute values, the root-sum-squares, the root-mean-squares, and/or the decimation of the spectral magnitudes is ultimately used to determine the inertial power and to identify the peak frequency. Cadence circuit 100 processes the inertial signal $S_i$ as disclosed herein to determine a user cadence C. Input/output interface 16 provides input from the user to the cadence circuit, and outputs the determined cadence C. It will be appreciated that input/output interface 16 may include a display, a keyboard or other data entry device, and/or a transceiver for transmitting the cadence to a remote device. Alternatively or additionally, the input/output interface 16 may provide the cadence to the display, a database, a processor, and/or a processing function. FIG. 3 shows an exemplary method 200 that may be implemented by the cadence measurement system 10 to determine a user cadence C. After the cadence circuit 100 receives the inertial signal $S_i$ from the inertial sensor 14a (block 210), the cadence circuit 100 determines a peak frequency $f_p$ based on $S_i$ (block 220). The peak frequency $f_p$ represents the frequency component of the inertial signal $S_i$ having the largest amplitude. The cadence circuit 100 subsequently applies the peak frequency $f_p$ to one or more frequency threshold comparisons (block 230). Based on the frequency threshold comparisons, the cadence circuit 100 determines the user cadence C (block 240).

Figure 4:
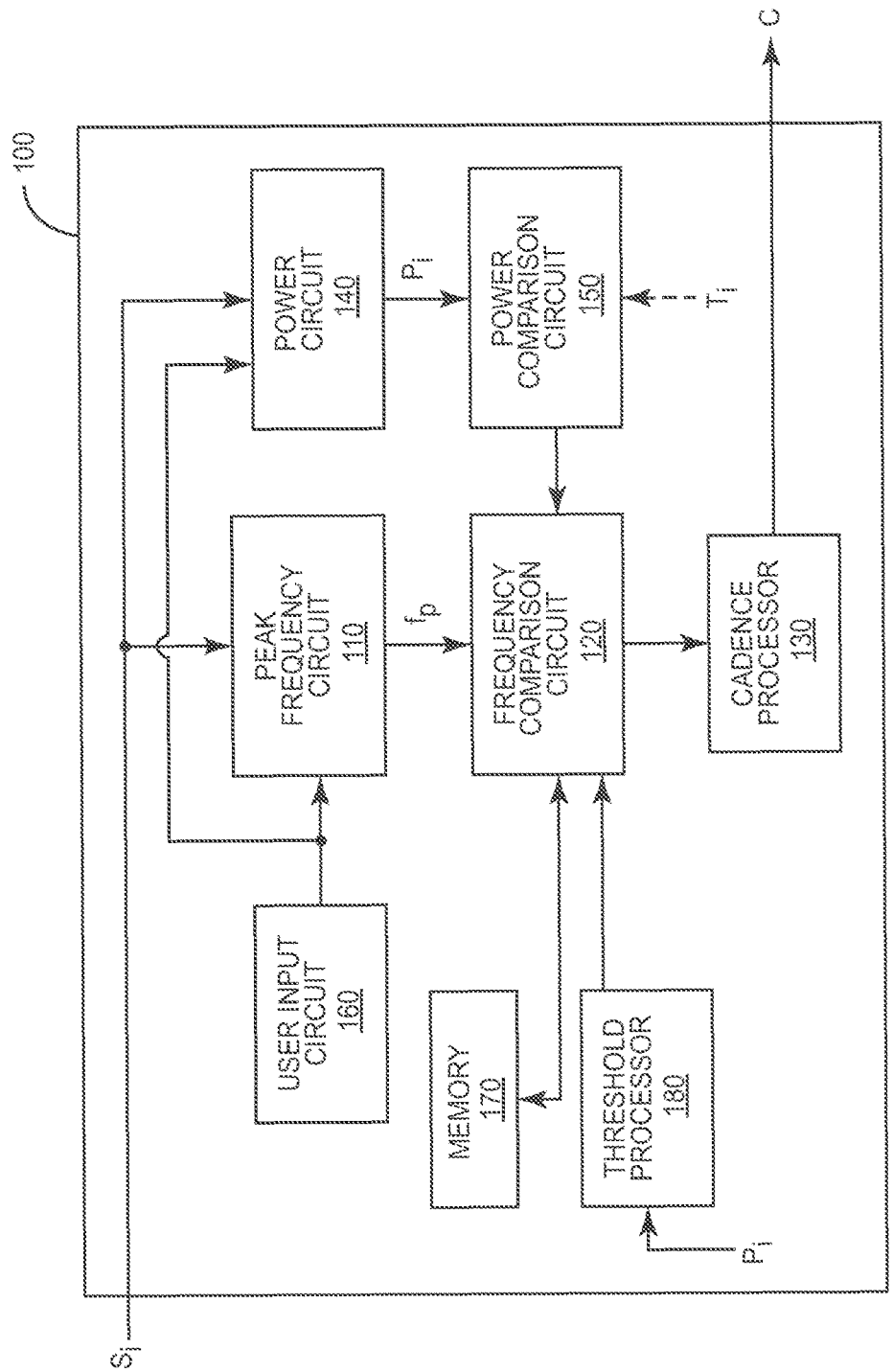
FIG. 4 shows a block diagram of an exemplary cadence circuit.

FIG. 4 shows a block diagram of an exemplary cadence circuit 100 configured to determine the user cadence from the inertial signal output by the inertial sensor 14a. Cadence circuit 100 comprises a peak frequency circuit 110, a frequency comparison circuit 120, and a cadence processor circuit 130. Peak frequency circuit 110 determines the peak frequency of the input inertial signal. The frequency comparison circuit 120 applies the peak frequency to one or more frequency threshold comparisons. The cadence processor circuit 130 determines the user cadence based on the peak frequency and the one or more frequency threshold comparisons.

The peak frequency circuit 110 identifies the frequency component of the inertial signal having the largest signal amplitude. In one exemplary embodiment, Peak frequency circuit 110 may achieve this goal by performing a frequency transform of the inertial signal to determine a spectral signal. The peak frequency circuit 110 then identifies the frequency component of the spectral signal having the largest amplitude as the peak frequency. It will be appreciated that other means, e.g., phase-locked loop, pulse picking, or time-domain implementations, may be used to determine the peak frequency.

Figure 5:
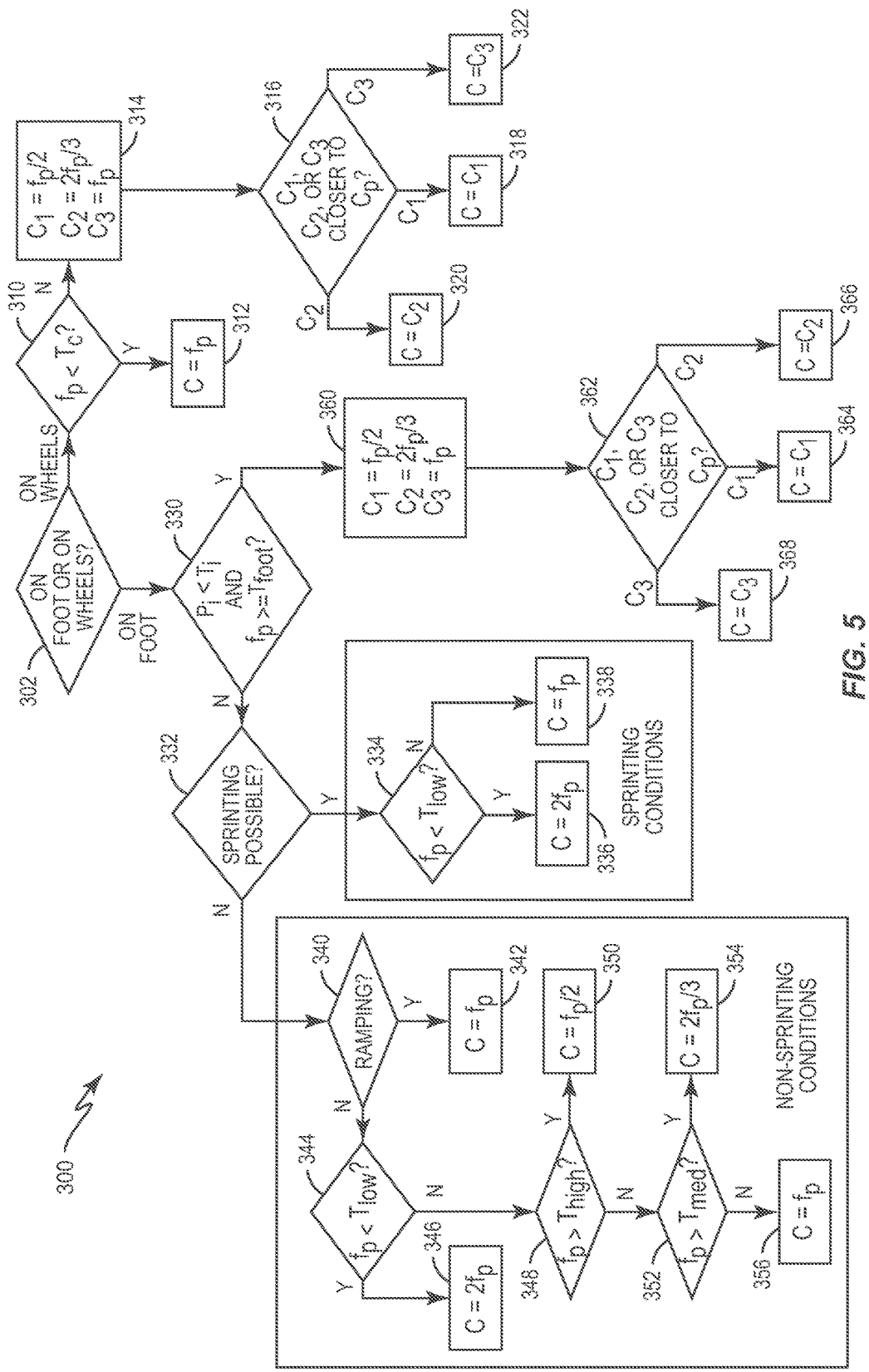
FIG. 5 shows a more detailed process for determining a user cadence from data provided by an inertial sensor according to one exemplary embodiment.

The frequency comparison circuit 120 applies the peak frequency to one or more frequency threshold comparisons. The frequency peak often corresponds directly to the user cadence. However, in some instances, the user cadence is some harmonic factor of the peak frequency. Empirical research shows the peak frequency is often twice, half, or three-halves the user cadence. As shown in FIG. 5, when sprinting is possible the typical walking harmonics are $2 f_p$, $\frac{3}{2} f_p$, or $\frac{1}{2} f_p$ and the typical running harmonics are $\frac{1}{2} f_p$. For example, harmonics at $2 f_p$ and $\frac{3}{2} f_p$ often occur when the user walks, but not when the user runs. Thus, the cadence may actually be $\frac{1}{2} f_p$ or $\frac{2}{3} f_p$, respectively. When the user runs, harmonics at $\frac{1}{2} f_p$ often occur. Thus, the cadence in this scenario may actually be $2 f_p$, $\frac{2}{3} f_p$, or $\frac{1}{2} f_p$. Thus, the cadence circuit 100 must determine which harmonic factor, if any, is applicable to determining the current user cadence.

The frequency threshold comparisons applied by the frequency comparison circuit 120 as disclosed herein solve this problem using one or more threshold comparisons, where the thresholds are determined based on a previous user cadence, an inertial power of the inertial signal, user activity parameters, user information, and/or empirical values. It will be appreciated that different harmonic factors and/or thresholds may apply depending on whether the user is sprinting, walking, running, ramping up from a low frequency value, cycling, etc. For example, harmonic factors due to arm swing, head bobbing, etc., impact the user cadence differently depending on how the user is moving, e.g., whether the user is running or walking. Thus, the cadence circuit 100 may optionally comprise a power circuit 140, a power comparison circuit 150, a user input circuit 160, a memory 170, and/or a threshold processor circuit 180 that determine and/or provide the various harmonic factors and thresholds necessary to determine the user cadence.

The power circuit 140 is configured to determine the inertial power $P_i$ of the inertial signal. To that end, the power circuit 140 may compute the inertial power in the time domain, e.g., using the root mean square, or in the frequency domain, e.g., using the amplitude of a spectral peak. The power comparison circuit compares $P_i$ to an inertial power threshold $T_i$ to facilitate the determination of whether the user is running or walking. User input circuit 160 receives input from the user. The user input may be used to determine one or more user activity parameters, e.g., whether the user is on foot or on wheels, whether sprinting is possible, etc. Threshold processor circuit 180 is configured to determine one or more of the thresholds used by the frequency comparison circuit 120, including any frequency thresholds used to determine a running cadence, a walking cadence, a cycling cadence, etc., and the power threshold used by the power comparison circuit 150. Memory 170 stores any predetermined thresholds, one or more previously determined cadences $C_p$, the various harmonic factors used by the cadence processor circuit 130, and any other information or software necessary for successful operation of the cadence circuit 100.

FIG. 5 shows an exemplary detailed process 300 executed by the cadence circuit 100 to determine the user cadence C. As shown by FIG. 5, cadence circuit 100 determines the user cadence based on the peak frequency and one or more frequency threshold comparisons. In exemplary embodiments, the cadence circuit 100 determines a user activity parameter, and determines the user cadence based on the frequency threshold comparison(s) and the user activity parameter. For example, the user activity parameter may identify whether the user is on foot or on wheels (block 302). When on wheels, the frequency comparison circuit 120 compares the peak frequency $f_p$ to a cycling threshold $T_c$, which may be fixed or variably determined based on an inertial power of the inertial signal (block 310). When $f_p < T_c$, the cadence processor circuit 130 sets the cadence equal to the peak frequency (block 312). Otherwise, the cadence processor circuit 130 generates two or more test cadences, and sets the user cadence equal to the test cadence closest to a previous user cadence (blocks 314-322). For example, the cadence processor circuit 130 may generate three test cadences: $C_1 = \frac{1}{2} f_p$, $C_2 = \frac{2}{3} f_p$, and $C_3 = f_p$ (block 314), and compare the three test cadences to a previous user cadence $C_p$ (block 316). If $C_1$ is closer to $C_p$ than $C_2$ or $C_3$ are, the cadence processor circuit 130 sets the user cadence equal to $C_1$ (block 318). If $C_2$ is closer to $C_p$ than $C_1$ or $C_3$ are, the cadence processor circuit 130 sets the user cadence equal to $C_2$ (block 320). If $C_3$ is closer to $C_p$ than $C_2$ or $C_1$ are, the cadence processor circuit 130 sets the user cadence equal to $C_3$ (block 322). While the example of FIG. 5 shows determining and using three specific test cadences, it will be appreciated that any two or more test cadences may be used.

When the user is on foot (block 302), the cadence processor circuit 130 sets the user cadence equal to the peak frequency divided by a harmonic factor, e.g., ½, 1, 3/2, 2, etc. More particularly, the cadence processor circuit 130 determines the user cadence based on frequency and power comparisons respectively performed by the frequency comparison circuit 120 and the power comparison circuit 150 (block 330). For example, when the inertial power $P_i$ is less than the inertial power threshold $T_i$ and $f_p \geq T_{foot}$, cadence processor circuit 130 generates two or more test cadences based on $f_p$ and two or more of the harmonic factors, and determines the user cadence based on the test cadences and a previous user cadence (blocks 360-368). For example, the cadence processor circuit 130 may generate three test cadences: $C_1 = \frac{1}{2} f_p$, $C_2 = \frac{2}{3} f_p$, and $C_3 = f_p$ (block 360), and compare the three test cadences to a previous user cadence $C_p$ (block 362). If $C_1$ is closer to $C_p$ than $C_2$ or $C_3$ are, the cadence processor circuit 130 sets the user cadence equal to $C_1$ (block 364). If $C_2$ is closer to $C_p$ than $C_1$ or $C_3$ are, the cadence processor circuit 130 sets the user cadence equal to $C_2$ (block 366). If $C_3$ is closer to $C_p$ than $C_2$ or $C_1$ are, the cadence processor circuit 130 sets the user cadence equal to $C_3$ (block 368). While the example of FIG. 5 shows determining and using three specific test cadences, it will be appreciated that any two or more test cadences may be used.

However, when the $P_i \geq T_i$ and/or $f_p < T_{foot}$, the cadence processor circuit 130 determines the user cadence based on frequency threshold comparison(s) and a sprinting user activity parameter, which indicates whether sprinting conditions are possible (blocks 332-356). More particularly, when $P_i \geq T_i$ and/or $f_p < T_{foot}$, the cadence processor circuit 130 determines whether sprinting conditions are possible based on user input (block 332). For example, the user may select an activity mode, e.g., walking, slow or low impact aerobics, high impact aerobics, running, etc. from a menu of options. Based on the selected activity mode, the cadence processor circuit 130 determines whether sprinting conditions are possible. For example, when the user selects slow aerobics, the cadence processor circuit 130 determines that sprinting is not possible. Alternatively, when the user selects running, the cadence processor circuit 130 determines that sprinting is possible. If sprinting conditions are possible, the cadence processor circuit 130 determines the user cadence based on a comparison between $f_p$ and a low frequency threshold $T_{low}$ under sprinting conditions (blocks 334-338). When $f_p < T_{low}$, the cadence processor circuit 130 sets the user cadence equal to the peak frequency divided by the ½ harmonic factor, e.g., equal to twice the peak frequency (block 336). Otherwise, the cadence processor circuit 130 sets the user cadence equal to the peak frequency (block 338).

If sprinting conditions are not possible, the cadence processor circuit 130 determines the user cadence based on multiple frequency threshold comparisons under non-sprinting conditions (blocks 340-356). More particularly, the cadence processor circuit applies the peak frequency to multiple thresholds based on whether the peak frequency is ramping up from a low frequency value (block 340), and determines the user cadence based on that ramping information and the frequency threshold conditions (blocks 342-356). While not required, in some exemplary embodiments, the low frequency value is zero. During non-sprinting conditions when the peak frequency is ramping up from a low frequency value, the cadence processor circuit 130 sets the user cadence equal to the peak frequency (block 342).

However, during non-sprinting conditions when the peak frequency is not ramping up from a low frequency value, the cadence processor circuit 130 determines the user cadence based on multiple peak frequency threshold comparisons determined by the frequency comparison circuit 120 under non-sprinting conditions relative to a low frequency threshold $T_{low}$, an intermediate frequency threshold $T_{med}$, and a high frequency threshold $T_{high}$, where $T_{low} < T_{med} < T_{high}$ (blocks 344-356). More particularly, under these conditions when $f_p < T_{low}$ (block 344), the cadence processor circuit 130 sets the user cadence equal to the peak frequency divided by the ½ harmonic factor, e.g., equal to twice the peak frequency (block 346). When $f_p \geq T_{low}$ and $f_p > T_{high}$ (blocks 344 and 348), the cadence processor circuit 130 sets the user cadence equal to the peak frequency divided by the 2 harmonic factor, e.g., equal to half the peak frequency (block 350). When $f_p \geq T_{low}$ and $f_p \leq T_{high}$ and $f_p > T_{med}$ (blocks 344, 348, and 352), the cadence processor circuit 130 sets the user cadence equal to the peak frequency divided by the 3/2 harmonic factor, e.g., equal to two-thirds the peak frequency (block 354). Otherwise, the cadence processor circuit 130 sets the user cadence equal to the peak frequency (block 356).

As discussed herein, the cadence circuit 100 determines the user cadence based on one or more frequency threshold comparisons. Each frequency threshold, as well as the inertial power threshold, may be determined empirically or based on one or more parameters, e.g., a previous user cadence, an inertial power, user information, and/or a user activity parameter. For example, the cycling threshold $T_c$ and/or the foot threshold $T_{foot}$ may be determined empirically based on observation, and/or based on user input information, user activity parameter, and/or the inertial power. In one exemplary embodiment, for example, the foot threshold may be determined according to:

$$T_{foot} = 120 + 40 \frac{P_i}{T_i}. \tag{1}$$

An exemplary cycling threshold $T_c$ is 100 revolutions per minute, while an exemplary foot threshold $T_{foot}$ is 145 steps per minute. The inertial power threshold and/or the low threshold may be determined empirically and/or based on user information, e.g., the user's weight, shoe sole compliance information, etc., the inertial power, a previous user cadence, and/or user activity parameters. In one exemplary embodiment, $T_{low}=60$ (a constant). It has been shown, for example, that the low frequency threshold is more accurate when determined as a function of the inertial power. For example, when $P_i \leq T_i$, the low threshold may be determined based on the inertial power when according to:

$$T_{low} = 60 + 20\frac{P_i}{T_i}. \qquad (2)$$

When $P_i > T_i$, alternatively, $T_{low}$ may be set equal to 80. In another exemplary embodiment, the low threshold may be determined based on the previous user cadence according to:

$$T_{low} = 0.6 C_p. \qquad (3)$$

It will be appreciated that different values for $T_{low}$ may be used for different scenarios. Thus, a combination of the above-disclosed options may be selectively used depending on the different scenarios, e.g., whether $P_i > T_i$. Similarly, the intermediate and high thresholds may be determined based on a previous user cadence and/or the inertial power. For example, the intermediate and high thresholds may be determined as a function of the previous user cadence and a sprint factor. The sprint factor for the intermediate threshold may be determined empirically, e.g., based on 1.75 times the previous user cadence. The sprint factor for the intermediate threshold may also be determined empirically, e.g., based on 1.4 times the previous user cadence. It will be appreciated that each threshold may be fixed or variable. It will also be appreciated that the frequency thresholds (e.g., $T_c$, $T_{foot}$, $T_{low}$, $T_{med}$, $T_{high}$) and the inertial power threshold ($T_i$) discussed herein are exemplary and non-limiting; other thresholds may be used depending on the system configuration, the information available to the cadence circuit 100, etc.

The user cadence method and apparatus disclosed herein accurately determines a user cadence for a wide range of circumstances and environments. Further, because the user may wear the hardware necessary to implement this invention, the invention disclosed herein is applicable for any user activity, including cycling, walking, running, athletic training, sports, aerobics, weight lifting or any other repetitive exercises, jumping, etc.

Figure 6A:
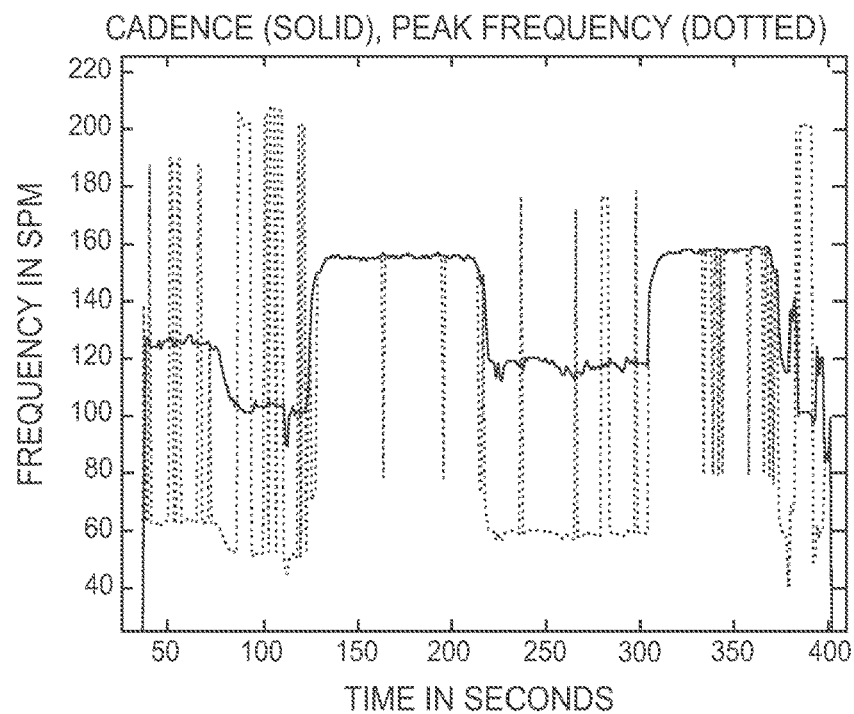
FIGS. 6A and 6B show simulated results associated with the disclosed solution.
Figure 6B:
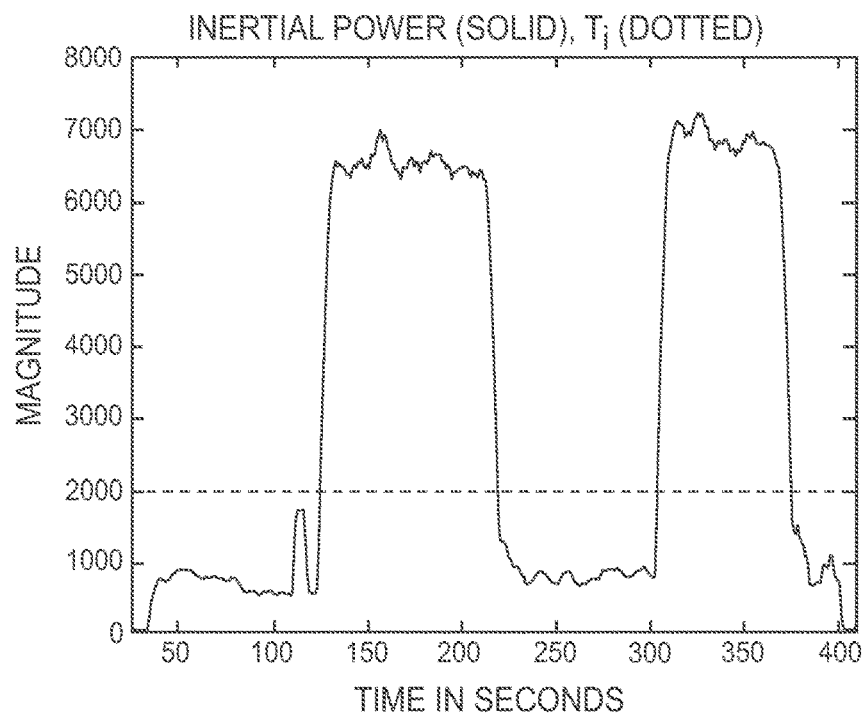

FIGS. 6A and 6B show simulated results for one exemplary implementation of the cadence measurement system disclosed herein. The plots shown in FIGS. 6A and 6B are generated from the same data set produced by an individual running and walking on a treadmill. FIG. 6A shows the user cadence with respect to time as computed according to FIG. 5 using the spectral peak frequency provided by the inertial sensor. FIG. 6B shows the inertial power output by the inertial sensor with respect to time. FIG. 6B also shows an exemplary inertial power threshold of 2000, which is used to determine whether the user is running or walking/resting. The circuits for the y-axis circuits Figure B are "g's" scaled by a systematic multiplier, where 1 g is the force of gravity on Earth at sea level. As shown by FIGS. 6A and 6B, the user is running from 125-215, seconds and from 300-375 seconds. Thus, in these regions, user cadence method and apparatus disclosed herein avoids mistaking the peak frequencies above 145 steps per minute as 2× or ³⁄₂× harmonics. The 40-70 seconds region shows ³⁄₂× and ½× harmonics, the 80-120 seconds region shows 2× and ½× harmonics, and the 125-215 seconds region shows ½× harmonics. All of these harmonics, when divided by the corresponding harmonic factor as disclosed herein, produce the correct user cadence.

In some embodiments, the cadence measurement system 10 may also comprise additional sensors. For example, the cadence measurement system 10 may include additional physiological sensors 14b, e.g., blood flow (photoplethysmography (PPG)), body temperature, and/or heart rate sensors.

In some embodiments, a noise circuit 18 (not shown) may be included to remove or otherwise attenuate cadence-related motion artifact noise from a physiological signal based on the determined user cadence output by the cadence circuit 100. For example, the determined cadence frequency may be selectively removed from the frequency spectrum of the outputs of one or more of the sensors 14 so that higher-quality sensor outputs are achieved with substantially attenuated motion artifacts.

In some embodiments, the sensor 14 may comprise an opto-mechanical sensor, comprising at least one optical emitter and one optical detector, such that inertial changes and cadence can be detected by the spectral characteristics of the opto-mechanical sensor output. In such embodiments, the thresholds described herein may be adapted when applied to the opto-mechanical sensor to account for differences in the sensing mechanism between an opto-mechanical sensor and an accelerometer, thereby generating an accurate measurement of cadence. In some embodiments, the opto-mechanical sensor may also be configured to shine light at the skin and detect light scattered from or through the skin to produce an output signal comprising both photoplethysmography components and inertial components. In such embodiments, the cadence measurement generated by the opto-mechanical sensor can be removed from the opto-mechanical sensor output to provide a second output having a cleaner photoplethysmography signal with substantially attenuated motion artifacts from cadence.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A method of determining a user cadence from an inertial signal generated by an inertial sensor disposed in a device secured to at least some portion of an ear of a user, the inertial signal comprising one or more frequency components, the method comprising:

determining, using a peak frequency circuit disposed in the device and operatively connected to the inertial sensor, a spectral signal based on a frequency transform of the inertial signal generated by the inertial sensor responsive to limb movement of the user;

determining, using the peak frequency circuit, a peak frequency of the spectral signal, said peak frequency corresponding to a frequency component of the inertial signal having a largest amplitude;

determining, using a cadence processor disposed in the device and operatively connected to a frequency comparison circuit, at least one frequency threshold for one or more frequency thresholds based on a previous user cadence of the user;

comparing, using the frequency comparison circuit disposed in the device and operatively connected to the peak frequency circuit, the peak frequency to at least one of the one or more frequency thresholds;

determining, using the cadence processor, the user cadence based on the peak frequency and the one or more frequency threshold comparisons, said user cadence representing a movement of one or more limbs of the user; and outputting the determined user cadence to an output circuit disposed in the device and operatively connected to the cadence processor.

2. The method of claim 1 wherein determining the user cadence comprises calculating the user cadence based on the peak frequency and the previous user cadence when the peak frequency exceeds a frequency threshold from the at least one of the one or more frequency thresholds.

3. The method of claim 1 wherein determining the user cadence comprises setting the user cadence equal to the peak frequency divided by a harmonic factor when the peak frequency is less than a frequency threshold from the at least one of the one or more frequency thresholds.

4. The method of claim 3 wherein the harmonic factor comprises one of ½, 1, 3/2, and 2.

5. The method of claim 1 further comprising:
determining, using a power circuit disposed in the device and operatively connected to the inertial sensor, a power of the inertial signal, said power of the inertial signal encompassing a plurality of the one or more frequency components of the inertial signal; and
comparing, using a power comparison circuit disposed in the device and operatively connected to the power circuit and the frequency comparison circuit, the power to a power threshold;
wherein determining the user cadence further comprises determining the user cadence based on the comparison between the power and the power threshold.

6. The method of claim 1 further comprising determining, using the cadence processor, whether the peak frequency is ramping up from a first frequency value, wherein determining the user cadence further comprises determining the user cadence based on whether the peak frequency is ramping up from the first frequency value.

7. The method of claim 1 further comprising:
determining, using a power circuit disposed in the device, a power of the inertial signal, said power of said inertial signal encompassing a plurality of the one or more frequency components of the inertial signal;
comparing, using a power comparison circuit disposed in the device and operatively connected to the power circuit and the frequency comparison circuit, the power to a power threshold; and
wherein determining the user cadence comprises determining the user cadence based on the peak frequency and the previous user cadence when the power is less than the power threshold and the peak frequency exceeds a frequency threshold from the at least one of the one or more frequency thresholds.

8. The method of claim 1 further comprising:
determining, using a power circuit disposed in the device, a power of the inertial signal, said power of said inertial signal encompassing a plurality of the one or more frequency components of the inertial signal; and
comparing, using a power comparison circuit disposed in the device and operatively connected to the power circuit and the frequency comparison circuit, the power to a power threshold; and
determining, using the cadence processor, whether sprinting is possible based on user input;
if sprinting is possible, determining the user cadence based on the one or more frequency threshold comparisons under sprinting conditions when the power exceeds the power threshold or the peak frequency is less than a frequency threshold from the at least one of the one or more frequency thresholds; and
if sprinting is not possible, determining the user cadence based on the one or more frequency threshold comparisons under non-sprinting conditions when the power exceeds the power threshold or the peak frequency is less than the frequency threshold from the at least one of the one or more frequency thresholds.

9. The method of claim 1 further comprising determining, using a threshold processor disposed in the device and operatively coupled to the frequency comparison circuit, at least one frequency threshold from the one or more frequency thresholds based on a power of the inertial signal, said power of said inertial signal encompassing a plurality of the one or more frequency components of the inertial signal.

10. The method of claim 1 further comprising determining, using a threshold processor disposed in the device and operatively coupled to the frequency comparison circuit, at least one frequency threshold from the one or more frequency thresholds based on an empirical value.

11. The method of claim 1 further comprising determining, using a user input circuit disposed in the device and operatively connected to the peak frequency circuit, a user activity parameter based on user input, wherein determining the user cadence comprises determining the user cadence based on the user activity parameter and the one or more frequency threshold comparisons.

12. The method of claim 1 wherein the inertial sensor comprises at least one of an accelerometer, a Micro-Electro-Mechanical System (MEMS) device, an optical sensor, a gyroscope, an opto-mechanical sensor, a blocked channel sensor, a capacitive sensor, and a piezoelectric sensor.

13. The method of claim 1 further comprising attenuating, using a noise circuit disposed in the device and operatively connected to the cadence processor, motion artifacts from a physiological signal proximate in frequency to the determined user cadence.

14. A cadence measurement system disposed in a device configured to secure to at least some portion of an ear of a user and configured to determine a user cadence, the cadence measurement system comprising:
an inertial sensor disposed in the device and configured to output an inertial signal responsive to limb movement of the user, said inertial signal comprising one or more frequency components;
a cadence circuit disposed in the device and operatively connected to the inertial sensor, said cadence circuit comprising:
a peak frequency circuit operatively connected to the inertial sensor and configured to determine:
a spectral signal based on a frequency transform of the inertial signal; and
a peak frequency of the spectral signal, said peak frequency corresponding to a frequency component of the inertial signal having a largest amplitude;
a cadence processor operatively coupled to the peak frequency circuit and configured to determine at least one frequency threshold for one or more frequency thresholds based on a previous user cadence of the user;
a frequency comparison circuit operatively coupled to the peak frequency circuit and the cadence processor, the frequency comparison circuit configured to compare the peak frequency to at least one of the one or more frequency thresholds; and wherein the cadence processor is further configured to determine the user cadence based on the peak frequency and the one or more frequency threshold comparisons, said user cadence representing a movement of one or more limbs of the user; and an output circuit disposed in the device and operatively connected to the cadence circuit, the output circuit configured to output the determined user cadence.

15. The cadence measurement system of claim 14 wherein the cadence circuit further comprises a memory operative to store the previous user cadence, wherein the cadence processor determines the user cadence by calculating the user cadence based on the peak frequency and the previous user cadence when the peak frequency exceeds a frequency threshold from the one or more frequency thresholds.

16. A method of determining a user cadence from an inertial signal generated by an inertial sensor disposed in a device secured to at least some portion of an ear of a user, the inertial signal comprising one or more frequency components, the method comprising:

determining, using a peak frequency circuit disposed in the device and operatively connected to the inertial sensor, a spectral signal based on a frequency transform of the inertial signal generated by the inertial sensor responsive to limb movement of the user;

determining, using the peak frequency circuit, a peak frequency of the spectral signal, said peak frequency corresponding to a frequency component of the inertial signal having a largest amplitude;

comparing, using a frequency comparison circuit disposed in the device and operatively connected to the peak frequency circuit, the peak frequency to one or more frequency thresholds;

determining, using a power circuit disposed in the device and operatively connected to the inertial sensor, a power of the inertial signal, said power of said inertial signal encompassing a plurality of the one or more frequency components of the inertial signal;

comparing, using a power comparison circuit disposed in the device and operatively connected to the power circuit and the frequency comparison circuit, the power to a power threshold;

determining, using a cadence processor disposed in the device and operatively connected to the frequency comparison circuit, the user cadence based on the peak frequency, the one or more frequency threshold comparisons, and the comparison between the power and the power threshold, said user cadence representing a movement of one or more limbs of the user; and outputting the determined user cadence to an output circuit disposed in the device and operatively connected to the cadence processor.

17. The method of claim 16 further comprising determining, using a user input circuit disposed in the device and operatively connected to the peak frequency circuit, a user activity parameter based on user input, wherein determining the user cadence comprises determining the user cadence based on the user activity parameter, the peak frequency, the one or more frequency threshold comparisons, and the comparison between the power and the power threshold.

18. A cadence measurement system disposed in a device configured to secure at least some portion of an ear of a user and configured to determine a user cadence, the cadence measurement system comprising:

an inertial sensor disposed in the device and configured to output an inertial signal responsive to limb movement of the user, said inertial signal comprising one or more frequency components;

a cadence circuit disposed in the device and operatively connected to the inertial sensor, said cadence circuit comprising:

a peak frequency circuit operatively connected to the inertial sensor and configured to determine:

a spectral signal based on a frequency transform of the inertial signal; and a peak frequency of the spectral signal, said peak frequency corresponding to a frequency component of the inertial signal having a largest amplitude;

a frequency comparison circuit operatively connected to the peak frequency circuit and configured to compare the peak frequency to one or more frequency thresholds;

a power circuit operatively connected to the inertial sensor and configured to determine a power of the inertial signal, said power of said inertial signal encompassing a plurality of the one or more frequency components of the inertial signal;

a power comparison circuit operatively connected to the power circuit and the frequency comparison circuit, the power comparison circuit configured to compare the power to a power threshold;

a cadence processor operatively connected to the frequency comparison circuit and configured to determine the user cadence based on the peak frequency, the one or more frequency threshold comparisons, and the comparison between the power and the power threshold, said user cadence representing a movement of one or more limbs of the user; and an output circuit disposed in the device and operatively connected to the cadence circuit, the output circuit configured to output the determined user cadence.

* * * * *